United States Patent
Croom, Jr. et al.

(10) Patent No.: US 6,734,166 B1
(45) Date of Patent: May 11, 2004

(54) METHOD OF REDUCING ALUMINUM LEVELS IN THE CENTRAL NERVOUS SYSTEM

(75) Inventors: Warren J. Croom, Jr., Cary, NC (US); Brian M. Berg, Sanford, NC (US); Ian L. Taylor, Kiawah Island, SC (US)

(73) Assignees: North Carolina State University, Raleigh, NC (US); MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 09/499,980

(22) Filed: Feb. 8, 2000

(51) Int. Cl.$^7$ .................. A61K 38/16; A61K 38/10; A61K 38/05

(52) U.S. Cl. ............... 514/12; 514/2; 514/13; 514/14; 514/15; 514/16; 514/17; 530/300; 530/324; 530/325; 530/326; 530/327; 530/328; 530/329

(58) Field of Search .................. 514/12, 13, 14, 514/15, 16, 17, 2; 530/324–329, 309

(56) References Cited

U.S. PATENT DOCUMENTS

| | | | |
|---|---|---|---|
| 5,385,915 A | 1/1995 | Buxbaum et al. ........... 514/313 |
| 5,604,203 A | 2/1997 | Balasubramaniam ........ 514/12 |
| 5,663,192 A | * 9/1997 | Bruns et al. ................ 514/420 |
| 5,716,828 A | 2/1998 | Roses et al. .................... 435/6 |
| 5,912,227 A | 6/1999 | Coom, Jr. et al. ............ 514/12 |
| 5,916,869 A | 6/1999 | Croom, Jr. et al. ............. 514/2 |

FOREIGN PATENT DOCUMENTS

WO   WO-94/22467 A1   * 10/1994

OTHER PUBLICATIONS

Gulya et al., [D–Pen2, D–Pen5]enkephalin, a d opiod agonist, reduces aluminum content in the rat central nervous system, Neuroscience (1995) 66(2):499–506.*
Alom et al. 1990. Cerebrospinal Fluid Neuropeptide Y in Alzheimer's Disease. *Eur Neurol* 30:207–210.
Beal et al. 1986. Neuropeptide Y Immunoreactivity is Reduced in Cerebral Cortex in Alzheimer's Disease. *Annals of Neurology* 20:282–288.
Chan–Palay et al. 1985. Cortical Neurons Immunoreactive with Antisera Against Neuropeptide Y are Altered in Alzheimer's–Type Dementia. *The Journal of Comparative Neurology* 238:390–400.
Davies et al. 1990. A Quantitative Assessment of Somatostatin–like and Neuropeptide Y–like Immunostained Cells in the Frontal and Temporal Cortex of Patients with Alzheimer's Disease. *Journal of the Neurological Sciences* 96:59–73.

Edvinsson et al. 1993. Neuropeptides in Cerebrospinal Fluid of Patients with Alzheimer's Disease and Dementia with Frontotemporal Lobe Degeneration. *Dementia* 4:167–171.
Gabriel et al. 1996. Neuropeptide Deficits in Schizophrenia vs. Alzheimer's Disease Cerebral Cortex. *Biological Psychiatry* 39:82–91.
Heilig et al. 1995. Cerebrospinal Fluid Neuropeptides in Alzheimer's Disease and Vascular Dementia. *Biological Psychiatry* 38:210–216.
Koide et al. 1995. Plasma Neuropeptide Y is Reduced in Patients with Alzheimer's Disease. *Neuroscience Letters* 198:149–151.
Martel et al. 1990. Neuropeptide Y Receptor Binding Sites in Human Brain. Possible Alteration in Alzheimer's Disease. *Brain Research* 519:228–235.
Martignoni et al. 1992. Cerebrospinal Fluid Norepinephrine, 3–methoxy–4–hydroxyphenylglycol and Neuropeptide Y Levels in Parkinson's Disease, Multiple System Atrophy and Dementia of the Alzheimer Type. *J. Neural Transm Park Dis Dement Sect* 4:191–205.
Minthon et al. 1996. Correlation Between Clinical Characteristics and Cerebrospinal Fluid Neuropeptide Y Levels in Dementia of the Alzheimer Type and Frontotemporal Dementia. *Alzheimer Disease and Associated Disorders* 10:197–203.
Minthon et al. 1997. Somatostatin and Neuropeptide Y in Cerebrospinal Fluid: Correlations with Severity of Disease and Clinical Signs in Alzheimer's Disease and Frontotemporal Dementia. *Dementia and Geriatric Cognitive Disorders* 8:232–239.
Rao et al. 1999. Neuropeptide Y Structure is Modulated by Aluminium in the Hypothalamus. *Alzheimer's Reports* 2:99–103.
Unnerstall et al. 1989. Alterations in the Density of [$^{125}$I] Peptide YY Binding Sites in the Hippocampus in Alzheimer's Disease. *Society for Neuroscience Abstracts* 15:861 Abstract 344.19.
Wikkelsö et al. 1991. Neuropeptides in Cerebrospinal Fluid in Normal–Pressure Hydrocephalus and Dementia. *Eur Neurol* 31:88–93.
Berg, et al., Peptide YY Administration Decreases Brain Aluminum in the Ts65Dn Down Syndrome Mouse Model, *Growth, Development & Aging*, vol. 64, pp. 3–19 (2000).

* cited by examiner

*Primary Examiner*—Gabriele Bugaisky
(74) *Attorney, Agent, or Firm*—Myers, Bigel, Sibley & Sajovec, P.A.

(57) ABSTRACT

A method of reducing aluminum concentrations in the central nervous system of a subject (e.g., a patient afflicted with Alzheimer's disease or at risk of developing Alzheimer's disease) comprises administering to subject a PYY receptor agonist in an amount effective to reduce aluminum concentrations, levels or amounts in the central nervous system of the subject. Compositions useful for carrying out the method are also disclosed.

19 Claims, 1 Drawing Sheet

METHOD OF REDUCING ALUMINUM LEVELS IN THE CENTRAL NERVOUS SYSTEM

FIELD OF THE INVENTION

The present invention concerns methods of reducing aluminum levels, amounts or concentrations in the central nervous system in patients or subjects in need thereof, such as Alzheimer's disease patients or patients at risk of developing Alzheimer's disease.

BACKGROUND OF THE INVENTION

Alzheimer's disease is a devastating neurological disease that is characterized by progressive and increasing memory loss, followed by loss of control of limbs and bodily functions and eventual death. As the life expectancy in the United States and elsewhere has progressed, the number of individuals afflicted with Alzheimer's disease has grown accordingly. Currently, approximately 4 million Americans (one in five of those 75 to 84 years of age and nearly half of those 85 years old and older) are now afflicted. See Newsweek, pg 48 (Jan. 31, 2000).

A variety of treatments are in development for Alzheimer's disease, and a few have been introduced. For example, U.S. Pat. No. 5,935,781 to Poirier describes the treatment of Alzheimer's disease with cholinomimetic drugs, and U.S. Pat. No. 5,523,295 to Fasman describes the treatment of Alzheimer's disease by administering a silicon compound capable of interaction between aluminum and β-amyloid or neurofilament proteins. Nevertheless, there remains a need for new ways to treat Alzheimer's disease.

The Ts65Dn (Ts) mouse contains a trisomic segment of murine chromosome 16 (MMU 16) that extends from an anonymous DNA locus, just proximal to the beta amyloid precursor protein (β-APP), to the end of the long arm (Davisson et al., In: The Phenotypic Mapping of Down Syndrome and Other Aneuploid Conditions. (ed. C. J. Epstein), pp.117–133. New York, N.Y.: Wiley-Liss, Inc. (1993); Kola and Hertzog, *Genetics & Development* 8, 316–321 (1998)). Portions of the genes encoded on this segment are homologous to those within the "Down syndrome critical region", cytogenetically classified as band 21q22 of human chromosome 21 (Davisson et al., supra). Several studies have reported similarities between Ts mice and Down syndrome (DS) individuals (Davisson et al., supra; Escorihuela et al., *Neurosci. Lett.*, 199, 143–146 (1995); Reeves et al., 1995; Holtzman et al., *Proc. Natl. Acad. Sci USA*, 93, 13333–13338 (1996); Cefalu et al. *Growth Dev. & Aging*, 62, 47–59 (1998); Kola and Hertzog, supra).

Cefalu et al. (supra) reported the Ts mouse exhibited decreased efficiency of intestinal absorption, shorter and thinner intestinal villi, lower whole-body oxygen consumption, elevated plasma concentrations of phenylalanine, tyrosine, citrulline, ornithine and decreased concentrations of hydroxyproline. The branched chain amino acids (BCAA); leucine, isoleucine, and valine were significantly elevated in Ts mice when compared to controls. In addition, Cefalu et al. confirmed previous reports of hyperactivity (Davisson et al.,supra), and small body size (Holtzman et al.,supra) of Ts mice compared to their control littermates.

PYY is composed of 36 amino acids and is a member of the pancreatic polypeptide family (Taylor, *Growth Dev. & Aging*, 62, 47–59 (1989)). It has been proposed as the putative humoral agent in the "ileal brake" phenomenon (Taylor, supra; Pironi et al., *Gastroenterology*, 105, 733–739 (1993); Lin et al., *Gastroenterology*, 110, 1491–1495 (1996)), although recent publications have disputed this hypothesis (Raybould et al., *Regulatory Peptides*, 79, 125–130 (1999); Zhao et al., *Regulatory Peptides*, 79, 125–130. (1999)). Bird et al. *J. Anim. Sci.*, 74, 2523–2540 (1996) first described the ability of exogenous PYY to enhance intestinal glucose uptake and the apparent energetic efficiency of glucose uptake (APEE) in mice. Infusion of PYY to conscious dogs has enhanced small intestinal water and electrolyte absorption in the fasting state (Bilchik et al., *Gastroenterology*, 105, 1441–1448 (1993)) and nutrient absorption in the post prandial state (Bilchik et al., *Am. J. Surgery*, 167, 6, 570–574 (1994)).

There is a high incidence of Alzheimer's disease (AD) in DS persons over the age of 40 (Schupf et al., *Neurology*, 50, 991–995 (1998)). Some studies indicate the Ts mouse brain displays AD neuropathology (Holtzman et al., supra), while others do not (Reeves et al., *Nature Genetics*, 11, 177–184 (1995)). Elevated brain aluminum (Al) content is a putative risk factor for AD (Savory et al., *Journal of Toxicology and Environmental Health*, 48, 615–635 (1996)). Aluminum is thought to enter the body primarily through intestinal absorption (Rogers and Simon, *Age and Aging*, 28, 205–209 (1999)). A recent study has shown Down syndrome persons absorb more Al from their intestinal tract than diploid controls (Moore et al., *Biological Psychiatry*, 41, 488–492 (1997)). Aluminum levels have not been studied in Ts mice.

SUMMARY OF THE INVENTION

A first aspect of the present invention is a method of reducing aluminum concentrations, levels, or amounts in the central nervous system of a subject in need thereof. The method comprises administering to said subject a PYY receptor agonist in an amount effective to reduce aluminum concentrations, levels or amounts in the central nervous system of the subject.

A particular aspect of the present invention is a method of treating Alzheimer's disease in a subject in need thereof, comprising administering to the subject a PYY receptor agonist in a treatment effective amount (e.g., an amount effective to reduce aluminum levels in the brain of the subject, or reduce or slow aluminum uptake in the brain of the subject).

Administering steps herein may be carried out chronically or acutely (or situationally) by any suitable route, including but not limited to parenteral and oral administration, nasal and inhalation administration, etc.

PYY receptor agonists, this term including the pharmaceutically acceptable salts thereof, are sometimes referred to as "active compounds" or "active agents" herein. A still further aspect of the present invention is the use of such active agents for the preparation of a medicament for the treatment of Alzheimer's disease or inhibiting or reducing brain aluminum levels in a subject in need thereof.

A still further aspect of the present invention is a composition comprising, in combination, a first active agent for treating Alzheimer's disease and a second (i.e. different) active agent for treating Alzheimer's disease, wherein said first active agent is a PYY receptor agonist. The composition may further comprise a pharmaceutically acceptable carrier. The second active agent may be any suitable active agent, including but not limited to cholinomimetic drugs, nonsteroidal anti-inflammatory agents, histamine H2 receptor blocking agents, silicon compounds capable of interaction between aluminum and β-amyloid or neurofilament protein, and proteinase inhibitors. The second active agent may be a centrally active anticholinesterase such as tacrine. The composition may be provided in any suitable form, such as an oral dosage composition.

The present invention is explained in greater detail in the specification set forth below.

DETAILED DESCRIPTION OF PREFERRED EMBODIMENTS

Figure 1:
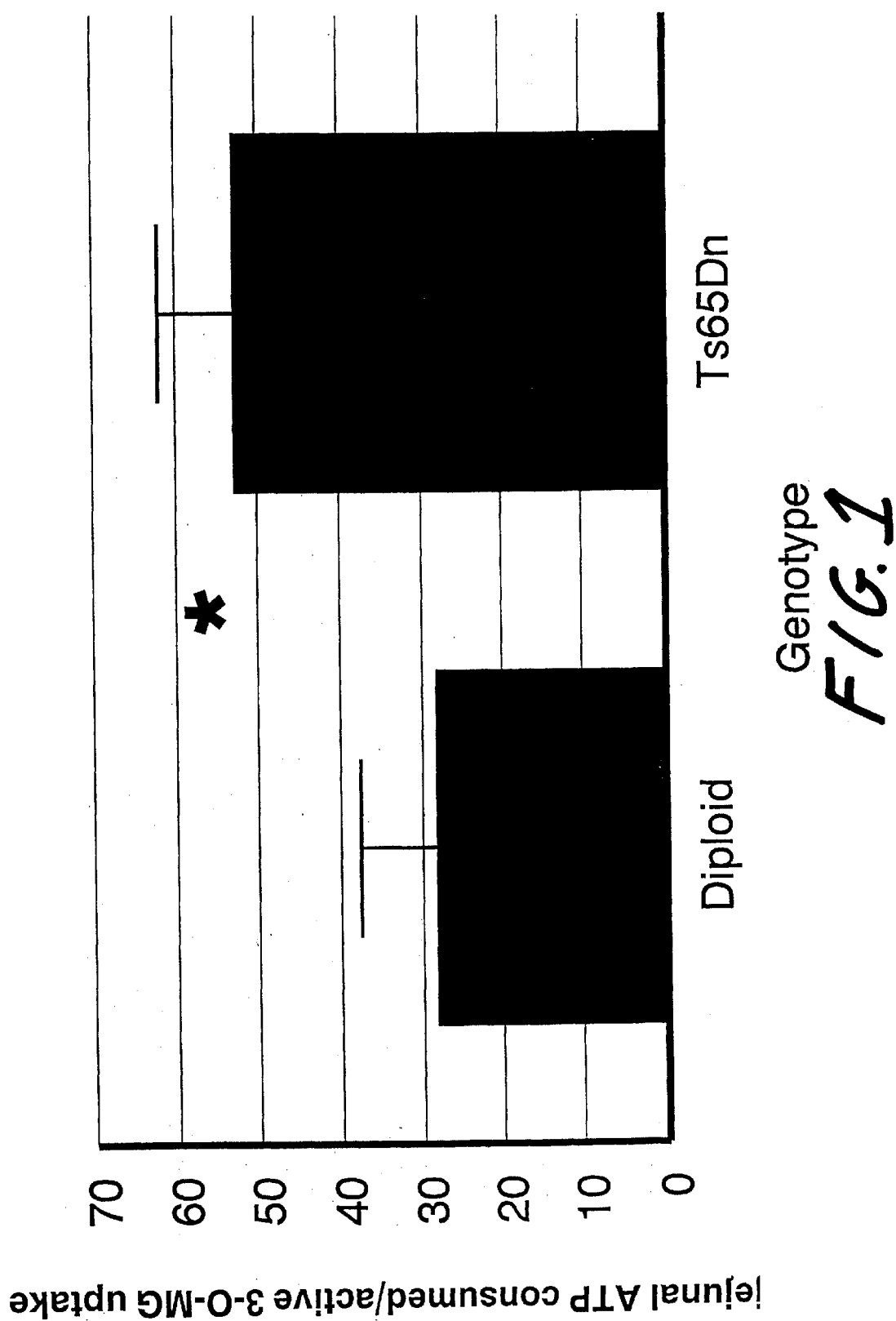
FIG. 1: Apparent energetic efficiency of active 3-O-methyl-D-glucose uptake. Jejunal ATP expended ($\eta$mol) per $\eta$mol active uptake of 3OMG in control and Ts65Dn mice. ATP expenditure data were calculated from total jejunal $O_2$ consumption values, assuming 5 $\eta$mol ATP synthesized per $\eta$mol $O_2$ consumed (Gill et al., *J. Nutr.*, 119, 1287–1299 (1989)) by wet jejunal tissue. 3-O-methyl-D-glucose active uptake values used in the calculations were expressed as $\eta$mol/min/mg wet jejunum. Values are mean ±SEM; n=19 diploid+saline, n=18 diploid+PYY, n=19 Ts65Dn+saline, n=18 Ts65Dn+PYY.*=p value$\leq$0.05.

The present invention is explained in greater detail in the specification set forth below. This information is not intended to be a detailed catalog of all variations within the scope of the present invention, but is instead intended to illustrate some particular embodiments thereof.

The disclosures of all U.S. Patent references cited herein are to be incorporated by reference herein in their entirety.

The term "treat" as used herein refers to any type of treatment or prevention that imparts a benefit to a patient afflicted with a disease or at risk of developing the disease, including improvement in the condition of the patient (e.g., in one or more symptoms), delay in the progression of the disease, delay the onset of symptoms or slow the progression of symptoms, etc. As such, the term "treatment" also includes prophylactic treatment of the subject to prevent the onset of symptoms. As used herein, "treatment" and "prevention" are not necessarily meant to imply cure or complete abolition of symptoms.

The term "central nervous system" as used herein refers to the brain and spinal column, with reduction of aluminum levels in the brain being particularly preferred.

The present invention may be used to treat or reduce aluminum levels in the central nervous system for any purpose, including but not limited to the treatment of Alzheimer's disease, the treatment of dialysis dementia, and the treatment of increased aluminum levels encountered in occupational diseases associated with the aluminum smelting industry and the like.

The present invention may be used to treat Alzheimer's disease (AD) in patients previously diagnosed with AD, or in patients considered to be at risk for AD. Risk of AD may be determined from family history, early cognitive examination, the detection of one or more Apolipoprotein E4 alleles (ApoE4) in the subject as described in U.S. Pat. No. 5,508,167 to Roses, or any other suitable technique (see, e.g., U.S. Pat. No. 5,297,562 to Potter; U.S. Pat. No. 5,972,638 to Tanzi et al.).

The term "Alzheimer's disease" as used herein is intended to encompass all types of Alzheimer's disease, including sporadic and familial AD, as well as late onset and early onset AD.

The term "pharmaceutically acceptable" as used herein means that the compound or composition is suitable for administration to a subject to achieve the treatments described herein, without unduly deleterious side effects in light of the severity of the disease and necessity of the treatment.

As discussed below, the active compounds of the present invention may optionally be administered in conjunction with other, different, active compounds useful in the treatment of the disorders or conditions described herein (e.g., Tacrine). The other compounds may be administered concurrently. As used herein, the word "concurrently" means sufficiently close in time to produce a combined effect (that is, concurrently may be simultaneously, or it may be two or more administrations occurring before or after each other).

The present invention is primarily concerned with the treatment of human subjects, but the invention may also be carried out on animal subjects, particularly mammalian subjects such as mice, rats, dogs, cats, pigs, cows, and horses, for veterinary purposes and/or for drug screening and drug development purposes.

1. Active Compounds

PYY (peptide tyrosine tyrosine) is a 36 amino acid peptide hormone produced by "L type" endocrine cells. See Boucher et al., *Regul. Pept.* 13, 283 (1986). PYY is a member of the pancreatic polypeptide family, which includes pancreatic polypeptide (PP) and neuropeptide Y (NPY), in addition to Peptide YY. PPY is released in response to feeding and has a variety of effects on the gastrointestinal tract, including inhibition of gastric acid secretion, inhibition of pancreatic exocrine secretion, delay of gastric emptying, and slowing of intestinal transit. See Savage et al., *Gut* 28, 166 (1987); Pironi et al., *Gastroenterology* 105, 733 (1993); Adrian et al., *Gastroenterology* 89, 494 (1985).

Binding studies using labelled PYY have demonstrated the presence of a PYY receptor in rat small intestine. Servin et al., *Endocrinology* 124, 692 (1989), used fragments of PYY peptide to study the structural requirements of peptides for competing with labelled PYY for binding to intestinal membranes, and reported that fragments of PYY acted as agonists of intact PYY, although at reduced biological activity.

Any mammalian PYY can be used to carry out the present invention. Examples include, but are not limited to, porcine and human PYY, which have the following amino acid sequences:

Porcine PYY: YPAKPEAPGEDASPEELSRYYASL-
    RHYLNLVTRQRY                    (SEQ. ID. NO. 1);

and

Human PYY: YPIKPEAPGEDASPEELNRYYASL-
    RHYLNLVTRQRY                    (SEQ. ID. NO. 2).

The amino acid sequence for dog and rat PYY is the same as porcine PYY.

In addition to the PYY peptides, PYY receptor agonists and antagonists, particularly agonists, may also be used in the methods of the present invention. As used herein "PYY agonist" means a substance which binds to the PYY receptor and induces the same physiologic responses as PYY. As used herein, "PYY antagonist" means a substance which binds to the PYY receptor and blocks the physiologic effect of PYY.

Methods of identifying receptor agonists and antagonists are well-known to those skilled in the art. PYY agonists and antagonists will typically bind to PYY receptors. Agonists will activate the PYY receptor. Activation can be assessed by changes to the receptor itself (e.g., conformational change, phosphorylation, internalization, etc.) or by induction of a physiological response, such as increased glucose absorption across the intestine without a concomitant increase in intestinal energy expenditure. Likewise, PYY receptor antagonists will block activation of the PYY receptor by PYY or other PYY receptor agonists. In general, such PYY receptor agonists and antagonists are PYY analogs.

An "analog" is a chemical compound similar in structure to a first compound, and having either a similar or opposite physiologic action as the first compound. With particular reference to the present invention, PYY peptide analogs are those compounds which, while not having the amino acid sequences of the PYY peptide, are capable of binding to the PYY receptor. Such analogs may be peptide or non-peptide analogs, including nucleic acid analogs, as described in further detail below.

In protein molecules which interact with a receptor, the interaction between the protein and the receptor must take place at surface-accessible sites in a stable three-dimensional molecule. By arranging the critical binding site residues in an appropriate conformation, peptides which mimic the essential surface features of the PYY peptide may be designed and synthesized in accordance with known techniques. International PCT Application WO 93/24515 (Cornell Research Foundation, Inc.) reports the cloning and identification of a human NPY/PYY receptor.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, *Science* 247, 28029 (1990); Rossmann, *Nature* 333, 392 (1988); Weis et al., *Nature* 333, 426 (1988); James et al., Science 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

Non-peptide mimetics of the peptides of the present invention are also an aspect of this invention. Non-protein drug design may be carried out using computer graphic modeling to design non-peptide, organic molecules able to bind to the PYY receptor. See, e.g., Knight, *BIO/Technology* 8, 105 (1990); Itzstein et al, *Nature* 363, 418 (1993) (peptidomimetic inhibitors of influenza virus enzyme, sialidase). Itzstein et al., *Nature* 363, 418 (1993), modeled the crystal structure of the sialidase receptor protein using data from x-ray crystallography studies and developed an inhibitor that would attach to active sites of the model; the use of nuclear magnetic resonance (NMR) data for modeling is also known in the art. See also Lam et al., *Science* 263, 380 (1994) regarding the rational design of bioavailable nonpeptide cyclic ureas that function as HIV protease inhibitors. Lam et al. used information from x-ray crystal structure studies of HIV protease inhibitor complexes to design nonpeptide inhibitors.

Analogs may also be developed by generating a library of molecules, selecting for those molecules which act as ligands for a specified target, and identifying and amplifying the selected ligands. See, e.g., Kohl et al., *Science* 260, 1934 (1993) (synthesis and screening of tetrapeptides for inhibitors of farnesyl protein transferase, to inhibit ras oncoprotein dependent cell transformation). Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News*, page 20, Feb. 7, 1994) and nonpeptide polymers (see, e.g., "peptoids" of Simon et al., *Proc. Natl. Acad. Sci. USA* 89, 9367 (1992)). See also U.S. Pat. No. 5,270,170 to Schatz; Scott and Smith, *Science* 249, 386–390 (1990); Devlin et al., *Science* 249, 404–406 (1990); Edgington, *BIO/Technology* 11, 285 (1993). Peptide libraries may be synthesized on solid supports, or expressed on the surface of bacteriophage viruses (phage display libraries). Known screening methods may be used by those skilled in the art to screen combinatorial libraries to identify PYY receptor ligands. Techniques are known in the art for screening synthesized molecules to select those with the desired activity, and for labelling the members of the library so that selected active molecules may be identified. See, e.g., Brenner and Lerner, *Proc. Natl. Acad. Sci. USA* 89, 5381 (1992) (use of genetic tag to label molecules in a combinatorial library); PCT US93/06948 to Berger et al., (use of recombinant cell transformed with viral transactivating element to screen for potential antiviral molecules able to inhibit initiation of viral transcription); Simon et al., *Proc. Natl. Acad. Sci. USA* 89, 9367 (1992) (generation and screening of "peptoids", oligomeric N-substituted glycines, to identify ligands for biological receptors); U.S. Pat. No. 5,283,173 to Fields et al., (use of genetically altered *Saccharomyces cerevisiae* to screen peptides for interactions).

As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, *BIO/Technology* 11, 285 (1993). U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai, Kenan and Keene, *Proc. Natl. Acad. Sci. USA* 89, 8864 (1992) and Tsai and Keene, *J. Immunology* 150, 1137 (1993). In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

Active compounds that may be used to carry out the present invention include, but are not limited to, the PYY analogs disclosed in U.S. Pat. No. 5,604,203 to Balasubramaniam, the disclosure of which is incorporated by reference herein in its entirety. The structures of such analogs are set forth below.

As set forth above and for convenience in describing this invention, the conventional and non-conventional abbreviations for the various amino acids are used. They are familiar to those skilled in the art; but for clarity are listed below:

Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=I=Isoleucine
Leu=L=Leucine
Lys=K=Lysine
Met=M=Methionine
Phe=F=Phenylalanine
Pro=P=Proline
Ser=S=Serine
Thr=T=Threonine
Trp=W=Tryptophan
Tyr=Y=Tyrosine
Val=V=Valine
Orn=Ornithine
Nal=2-napthylalanine
Nva=Norvaline
Nle=Norleucine
Thi=2-thienylalanine
Pcp=4-chlorophenylalanine
Bth=3-benzothienylalanine
Bip=4,4'-biphenylalanine
Tic=tetrahydroisoquinoline-3-carboxylic acid
Aib=aminoisobutyric acid
Anb=.alpha.-aminonormalbutyric acid
Dip=2,2-diphenylalanine
Thz=4-Thiazolylalanine All peptide sequences mentioned herein are written according to the usual convention whereby the N-terminal amino acid is on the left and the C-terminal amino acid is on the right. A short line (or no line) between two amino acid residues indicates a peptide bond.

Peptide YY analogs that may be used to carry out the present invention include compounds of Formula I:

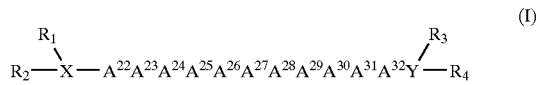

(I)

wherein:

X is a chain of 0–5 amino acids, inclusive, the N-terminal one of which is bonded to $R_1$ and $R_2$;

Y is a chain of 0–4 amino acids, inclusive, the C-terminal one of which is bonded to $R_3$ and $R_4$;

$R_1$ is H, C1–C12 alkyl (e.g., methyl), C6–C18 aryl (e.g., phenyl, naphthaleneacetyl), C1–C12 acyl (e.g., formyl, acetyl, and myristoyl), C7–C18 aralkyl (e.g., benzyl), or C7–C18 alkaryl (e.g., p-methylphenyl);

$R_2$ is H, C1–C12 alkyl (e.g., methyl), C6–C18 aryl (e.g., phenyl, naphthaleneacetyl), C1–C12 acyl (e.g., formyl, acetyl, and myristoyl), C7–C18 aralkyl (e.g., benzyl), or C7–C18 alkaryl (e.g., p-methylphenyl);

$A^{22}$ is an aromatic amino acid, Ala, Aib, Anb, N-Me-Ala, or is deleted;

$A^{23}$ is Ser, Thr, Ala, Aib, N-Me-Ser, N-Me-Thr, N Me-Ala, or is deleted;

$A^{24}$ is Leu, Ile, Val, Trp, Gly, Nle, Nva, Aib, Anb, N-Me-Leu, or is deleted;

$A^{25}$ is Arg, Lys, homo-Arg, diethyl-homo-Arg, Lys-.epsilon.-NH—R (where R is H, a branched or straight chain C1–C10 alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-.epsilon.-NH—R (where R is H, a branched or straight chain C1–C10 alkyl groups or an aryl group), Orn, or is deleted;

$A^{27}$ is an aromatic amino acid other than Tyr;

$A^{28}$ is Leu, Ile, Val, Trp, Nle, Nva, Aib, Anb, or N-Me-Leu;

$A^{29}$ is Asn, Ala, Gln, Gly, Trp, or N-Me-Asn;

$A^{30}$ is Leu, Ile, Val, Trp, Nle, Nva, Aib, Anb, or N-Me-Leu;

$A^{31}$ is Val, Leu, Ile, Trp, Nle, Nva, Aib, Anb, or N-Me-Val;

$A^{32}$ is Thr, Ser, N-Me-Ser, N-Me-Thr, or D-Trp;

$R_3$ is H, C1–C12 alkyl (e.g., methyl), C6–C18 aryl (e.g., phenyl, naphthaleneacetyl), C1–C12 acyl (e.g., formyl, acetyl, and myristoyl), C7–C18 aralkyl (e.g., benzyl), or C7–C18 alkaryl (e.g., p-methylphenyl); and $R_4$ is H, C1–C12 alkyl (e.g., methyl), C6–C18 aryl (e.g., phenyl, naphthaleneacetyl), C1–C12 acyl (e.g., formyl, acetyl, and myristoyl), C7–C18 aralkyl (e.g., benzyl), or C7–C18 alkaryl (e.g., p-methylphenyl), or a pharmaceutically acceptable salt thereof.

In particular embodiments, $A^{27}$ is Phe, Nal, Bip, Pcp, Tic, Trp, Bth, Thi, or Dip.

In particular embodiments X is $A^{17}$-$A^{18}$-$A^{19}$-$A^{20}$-$A^{21}$ wherein $A^{17}$ is Cys, Leu, Ile, Val, Nle, Nva, Aib, Anb, or N-Me-Leu;

$A^{18}$ is Cys, Ser, Thr, N-Me-Ser, or N-Me-Thr;

$A^{19}$ is Arg, Lys, homo-Arg, diethyl-homo-Arg, Lys-.epsilon.-NH—R (where R is H, a branched or straight chain C1–C10 alkyl group, or C6–C18 aryl group), Cys, or Orn;

$A^{20}$ is an aromatic amino acid, or Cys; and $A^{21}$ is an aromatic amino acid, Cys, or a pharmaceutically acceptable salt thereof.

In yet other particular embodiments, Y is $A^{33}$-$A^{34}$-$A^{35}$-$A^{36}$ wherein:

$A^{33}$ is Arg, Lys, homo-Arg, diethyl-homo-Arg, Lys-.epsilon.-NH—R (where R is H, a branched or straight chain C1–C10 alkyl group, or an aryl group), Cys, or Orn;

$A^{34}$ is Cys, Gln, Asn, Ala, Gly, N-Me-Gln, Aib, or Anb;

$A^{35}$ is Arg, Lys, homo-Arg, diethyl-homo-Arg, Lys-.epsilon.-NH—R (where R is H, a branched or straight chain C1–C10 alkyl group, or an aryl group), Cys, or Orn; and $A^{36}$ is an aromatic amino acid, Cys or a pharmaceutically acceptable salt thereof.

In specific embodiments, the active compound has the formula:

N-.alpha.-Ac-Ala-Ser-Leu-Arg-His-Phe-Leu-Asn-Leu-Val-Thr-Arg-Gln-Arg-Tyr-NH₂ (SEQ. ID. NO. 3);

H-Ala-Ser-Leu-Arg-His-Phe-Leu-Asn-Leu-Val-Thr-Arg-Gln-Arg-Tyr-NH₂ (SEQ. ID. NO. 4);

N-.alpha.-Ac-Ala-Ser-Leu-Arg-His-Trp-Leu-Asn-Leu-Val-Thr-Arg-Gln-Arg-Tyr-NH₂ (SEQ. ID. NO. 5);

N-.alpha.-Ac-Ala-Ser-Leu-Arg-His-Thi-Leu-Asn-Leu-Val-Thr-Arg-Gln-Arg-Tyr-NH₂ (SEQ. ID. NO. 6);

N-.alpha.-Ac-Tyr-Ser-Leu-Arg-His-Phe-Leu-Asn-Leu-Val-Thr-Arg-Gln-Arg-Tyr-NH₂ (SEQ. ID. NO. 7);

or a pharmaceutically acceptable salt thereof.

In another aspect, the invention may be carried out with analogs of peptide YY of Formula II:

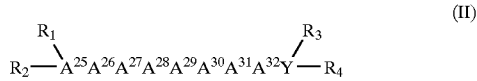
(II)

wherein the N-terminal amino acid is bonded to $R_1$ and $R_2$;

Y is a chain of 0–4 amino acids, inclusive, the C-terminal one of which is bonded to $R_3$ and $R_4$;

$R_1$ is H, C1–C12 alkyl (e.g., methyl), C6–C18 aryl (e.g., phenyl, napthaleneacetyl), C1–C12 acyl (e.g., formyl, acetyl, and myristoyl), C7–C18 aralkyl (e.g., benzyl), or C7–C18 alkaryl (e.g., p-methylphenyl);

$R_2$ is H, C1–C12 alkyl (e.g., methyl), C6–C18 aryl (e.g., phenyl, napthaleneacetyl), C1–C12 acyl (e.g., formyl, acetyl, and myristoyl), C7–C18 aralkyl (e.g., benzyl), or C7–C18 alkaryl (e.g., p-methylphenyl);

$A^{25}$ is Arg, Lys, homo-Arg, diethyl-homo-Arg, Lys-.epsilon.-NH—R (where R is H, a branched or straight chain C1–C10 alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-e-NH—R (where R is H, a branched or straight chain C1–C10 alkyl group, or an aryl group), Orn, or is deleted;

$A^{27}$ is an aromatic amino acid;

$A^{28}$ is Leu, Ile, Val, Trp, Nle, Nva, Aib, Anb, or N-Me-Leu;

$A^{29}$ is Asn, Ala, Gln, Gly, Trp, or N-Me-Asn;

$A^{30}$ is Leu, Ile, Val, Trp, Nle, Nva, Aib, Anb, or N-Me-Leu;

$A^{31}$ is Val, Ile, Trp, Nva, Aib, Anb, or N-Me-Val;

$A^{32}$ is Thr, Ser, N-Me-Ser, N-Me-Thr, or D-Trp;

$R_3$ is H, C1–C12 alkyl (e.g., methyl), C6–C18 aryl (e.g., phenyl, napthaleneacetyl), C1–C12 acyl (e.g., formyl, acetyl, and myristoyl), C7–C18 aralkyl (e.g., benzyl), or C7–C18 alkaryl (e.g., p-methylphenyl); and $R_4$ is H, C1–C12 alkyl (e.g., methyl), C6–C18 aryl (e.g., phenyl, napthaleneacetyl), C1–C12 acyl (e.g., formyl, acetyl, and myristoyl), C7–C18 aralkyl (e.g., benzyl), or C7–C18 alkaryl (e.g., p-methylphenyl), or a pharmaceutically acceptable salt thereof.

In particular embodiments of the foregoing A27 is Phe, Nal, Bip, Pcp, Tic, Trp, Bth, Thi, or Dip.

In particular embodiments of the foregoing Y is A33-A34-A35-A36 wherein

A33 is Arg, Lys, homo-Arg, diethyl-homo-Arg, Lys-.epsilon.-NH—R (where R is H, a branched or straight chain C1–C10 alkyl group, or C6–C18 aryl group), Cys, or Orn;

$A^{34}$ is Gln, Asn, Ala, Gly, N-Me-Gln, Aib, Cys, or Anb;

$A^{35}$ is Arg, Lys, homo-Arg, diethyl-homo-Arg, Lys-.epsilon.-NH—R (where R is H, a branched or straight chain C1–C10 alkyl group, or C6–C18 aryl group), Cys, or Orn; and $A^{36}$ is an aromatic amino acid, Cys, or a pharmaceutically acceptable salt thereof.

A Specific compound illustrative of the foregoing has the formula:

N-.alpha.-Ac-Arg-His-Phe-Leu-Asn-Leu-Val-Thr-Arg-Gln-Arg-Tyr-NH₂ (SEQ. ID. NO. 8).

In another aspect, the invention may be carried out with dimeric analogs of peptide YY. The dimer may be formed by either including two peptides of Formula I, two peptides of Formula II, or one peptide of Formula I and one peptide of Formula II. In one embodiment, the dimer is formed by utilizing a dicarboxylic acid linker capable of binding to a free amine, either primary or secondary, located within each peptide. See, e.g., R. Vavrek and J. Stewart, Peptides: Structure and Function 381–384 (Pierce Chemical Co. 1983). Examples of suitable dicarboxylic acid linkers are succinic acid, glutamic acid, and phthalic acid. In other embodiments, the dimer is formed by utilizing an amino acid linker capable of binding to a free amine group of one peptide and a free carboxyl group of the other peptide.

Preferably, the amino acid linker is a non .alpha.-amino acid. Examples of suitable amino acid linkers are amino-caproic acid and amino-valeric acid. In yet another embodiment, the dimer is formed by a disulfide bridge between cysteines located within each peptide. See, e.g., M. Berngtowicz and G. Piatsueda, Peptides: Structure and Function 233–244 (Pierce Chemical Co. 1985); F. Albericio, et al., Peptides 1990. 535 (ESCOM 1991).

In yet another aspect, the invention features analogs of Formula I or Formula II having at least one pseudopeptide bond between amino acid residues. By "pseudopeptide bond" is meant that the carbon atom participating in the bond between two residues is reduced from a carbonyl carbon to a methylene carbon, i.e., $CH_2$—NH; or less preferably that of CO—NH is replaced with any of $CH_2$—S, $CH_2$—$CH_2$, $CH_2$—O, or $CH_2$—CO. A pseudopeptide peptide bond is symbolized herein by ".PSI.". Preferably, the pseudopeptide bonds are located between one or more amino acid residues, e.g., $A^{28}$.PSI.$A^{29}$, $A^{29}$.PSI.$A^{30}$, $A^{30}$.PSI.$A^{31}$, $A^{31}$.PSI.$A^{32}$, $A^{32}$.PSI.$A^{33}$, $A^{33}$.PSI.$A^{34}$, $A^{34}$.PSI.$A^{35}$, or $A^{35}$.PSI.$A^{36}$. In addition, such pseudopeptide bond analogs can be used to form dimeric analogs as is described above. A detailed discussion of the chemistry of pseudopeptide bonds is given in Coy et al. (1 988) *Tetrahedron* 44:835–841.

The symbol X, Y, Z, $A^{22}$, $A^{23}$, $A^{24}$, and the like; and Ser, Leu or the like, as found in a peptide sequence herein stands for an amino acid residue, i.e., =N—CH(R)—CO— when it is at the N-terminus, or —NH—CH(R)—CO—N= when it is at C-terminus, or —NH—CH(R)—CO— when it is not at the N- or C-terminus, where R denotes the side chain (or identifying group) of an amino acid or its residue. For example, R is —CH2 COOH for Asp, R is —H for Gly, R is —$CH_2$OH for Ser, R is—CH3 for Ala and R is —$CH_2CH_2CH_2CH_2NH_2$ for Lys. Also, when the amino acid residue is optically active, it is the L-form configuration that is intended unless the D-form is expressly designated.

Peptides of the present invention may be made in accordance with techniques known in the art. Using accepted techniques of chemical synthesis, the peptide may be built up either from the N-terminus or, more typically, the C-terminus using either single amino acids or preformed peptides containing two or more amino acid residues. Particular techniques for synthesizing peptides include (a) classical methods in which peptides of increasing size are isolated before each amino acid or preformed peptide addition, and (b) solid phase peptide synthesis in which the peptide is built up attached to a resin such as a Merrifield resin. In these synthetic procedures, groups on the amino acids will generally be in protected form using standard protecting groups such as t-butoxycarbonyl. If necessary, these protecting groups are cleaved once the synthesis is complete. Other modifications may be introduced during or after the synthesis of the peptide. Peptides of the present invention may also be produced through recombinant DNA procedures as are known in the art.

The active compounds disclosed herein can, as noted above, be prepared and administered in the form of their pharmaceutically acceptable salts. Pharmaceutically acceptable salts are salts that retain the desired biological activity of the parent compound and do not impart excessive toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Other Active Agents and Combination Treatments

As noted above, subjects administered the PYY receptor agonists described above may also be administered other active compounds for the treatment of Alzheimer's disease. The combined benefit of the two different active compounds administered together may be additive, synergistic, or even less than additive so long as the combined treatment benefit to the patient is greater than the treatment benefit of either active agent given alone.

Other active agents useful in the treatment of Alzheimer's disease include, but are not limited to, cholinomimetic compounds (see, e.g., U.S. Pat. No. 5,935,781 to Poirier et al.), nonsteroidal anti-inflammatory agents and histamine H2 receptor blocking agents (see, e.g., U.S. Pat. No. 5,643, 960), silicon compounds capable of interaction between aluminum and β-amyloid or neurofilament proteins (see U.S. Pat. No. 5,523,295 to Fasman), estrogen replacement therapy agents (e.g., estrogen or estrogen receptor agonists) protease inhibitors (see, e.g., U.S. Pat. Nos. 6,017,887; 6,015,879; 5,596,241; and 5,714,471). All U.S. Patent references cited herein are to be incorporated by reference herein in their entirety.

A particularly preferred active agent for administering is combination with the PYY receptor agonist is acentrally active anticholinesterase such as tacrine (see, e.g., U.S. Pat. Nos. 5,698,224; 5,576,022; and 4,816,248), both of which may be administered orally, and both of which may be administered orally in a single combination dosage form.

3. Pharmaceutical Formulations

The active compounds described above may be formulated for administration in a pharmaceutical carrier in accordance with known techniques. See, e.g., Remington, *The Science And Practice of Pharmacy* ($9^{th}$ Ed. 1995).

Where the pharmaceutical formulation contains in combination both a PYY receptor agonist (or a pharmaceutically acceptable salt) and a second, different active agent (e.g., tacrine) for treating Alzheimer's disease, as described above, the pharmaceutical formulations are novel formulations. Other active agents can be included in the formulation in their known and recommended amounts.

In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, nasal, inhalation (e.g., to the lungs), buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for oral administration may be controlled release or osmotic dosage forms, as described in U.S. Pat. Nos. 5,576,022 and 5,698,244.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for nasal, parenteral, or inhalation administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the active compounds disclosed herein. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

The liposomal formulations containing the compounds disclosed herein, may be lyophilized to produce a lyophilizate which may be reconstituted with a pharmaceutically acceptable carrier, such as water, to regenerate a liposomal suspension.

Other pharmaceutical compositions may be prepared from the compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

4. Dosage and Routes of Administration

As noted above, the present invention provides pharmaceutical formulations comprising the active compounds (including the pharmaceutically acceptable salts thereof), in pharmaceutically acceptable carriers for oral, rectal, topical, buccal, nasal, inhalation (e.g., to the lungs) parenteral, intramuscular, intradermal, or intravenous, and transdermal administration.

The therapeutically effective dosage of any one active agent, the use of which is in the scope of present invention, will vary somewhat from compound to compound, and patient to patient (depending upon the age and condition of the subject), and will depend upon factors such as the age and condition of the patient and the route of delivery. Such dosages can be determined in accordance with routine pharmacological procedures known to those skilled in the art.

In general, the daily dose in the case of oral administration is typically in the range of 0.01 or 0.1 to 100 or 500 mg/kg body weight, and the daily dose in the case of parenteral (e.g., subcutaneous) administration is typically in the range of 0.0001 or 0.001 to 50 or 100 mg/kg body weight. Daily dosages may be administered in a single unit or multiple units each day.

Administration may be carried out on a chronic or acute basis. When the administering step is an acute administering step, the active agent may (for example) be given as a single dosage as above, or daily in the above dosages for a period of 2 days 5 days. Where the administering step is a chronic administrating step, the daily dosage will be given at least 3, 4 or 5 times a week (e.g., seven days a week) for a period of at least two weeks, at least a month, at least two months, or even at least six months or more. When a chronic dosage regimen is completed the patient may be reevaluated and the administration continued or modified as necessary.

When other active agents are administered in combination with the PYY receptor agonist, they may be given in their known or recommended amounts.

The present invention is illustrated further in the following non-limiting Examples.

EXAMPLES 1–2

Peptide YY Administration and Nutrient Digestibility, Intestinal Function, Blood Metabolites and Brain Aluminum in Ts65Dn Mice The objectives of these examples were to investigate the effects of exogenous PYY on nutrient digestibility, organ sizes, and the rate and efficiency of intestinal glucose and proline absorption in Ts mice and their diploid controls. Additionally, characterization of various intermediary metabolites and brain aluminum (Al) levels were determined to further evaluate the usefulness of Ts mice as a model for investigating metabolic and central nervous system degenerative diseases in Down syndrome.

A. Materials and Methods

Experimental design.

Mice were obtained from Dr. Muriel Davisson of the Jackson Laboratories, Bar Harbor, Me., 5 days prior to beginning the experiments. In both Trials 1 and 2, a randomized complete block design was utilized and included four treatments; a) diploid mice+saline; b) diploid mice+PYY; c) Ts mice+saline; d) Ts mice+PYY.

Animal care and diet.

All mice were cared for and treated according to the guidelines of the Institutional Animal Care and Use Committee of North Carolina State University. Mice used in Trial 1 were housed individually in Nalgene® brand metabolism cages (Mini Mitter Co., Inc., OR) in a climatically controlled room (23° C., 50–60% humidity) with a 12 h/12 h light:dark cycle. Mice were allowed three days adjustment to the cages before experimentation began. Mice had free access to food (LabDiet® NIH Rat and Mouse/Auto 6F5K52, St. Louis, Mo.) and water during the experimental period except for the 16 hours prior to euthanasia when no food was provided. Identical care was provided in Trial 2 except these mice were housed individually in polypropylene cages.

Trial 1.

Trial one consisted of two apparent digestibility trial replicates. Each replicate included 6 Ts (average age=1.8 months) and six diploid (average age=1.84 months) male mice and lasted 14 days. On the day of their arrival, both diploid and Ts mice were weighed and randomly assigned to both a cage location and treatment. On each experimental day, PYY (300 µg/kg body weight) or saline (0.9% NaCl) was administered subcutaneously (s.c.). Feed and water intakes and urine and feces outputs were measured daily. Feces and urine were collected and frozen for future analysis. Urine was acidified to a pH of 3–5 prior to freezing.

On day 13, mice were fasted 16 hours prior to tissue sample collection. Mice were sedated with $CO_2$ and then bled by cardiac puncture. Heparinized blood was centrifuged for five minutes and plasma stored in liquid nitrogen (−196° C.) for future analysis. Livers, brains and epididymal fat pads were dissected, weighed and stored at −20° C. The entire small intestine was removed by cutting at the pyloric and ileocecal sphincters. Excess mesentery and adipose tissue was carefully excised, and the resulting tissue's unstretched length and weight was recorded.

Fecal samples were thawed at room temperature and then ground into fine particles. Fecal dry matter percent was determined by drying at 80° C. for 48 hours. Fecal energy content was determined using a Parr adiabatic bomb calorimeter (Parr Instrument Company, Moline, Ill.). The procedures for conducting semi-automated nitrogen analysis and preparing standard nitrogen solutions and reagents were followed to determine fecal and urinary nitrogen concentrations (AOAC 1990, $15^{th}$ edition paragraph 976.06). One half gram of feces or one mL of urine were combined with one KJELTAB (3.9 g, 89.7% potassium sulfate, 10.3% cupric sulphate; Thompson and Capper Ltd., Cheshire, England) and 7.5 mL concentrated sulfuric acid in a 100 mL calibrated volumetric tube and digested at 375° C. in a Tecator DS-40 block digestor (Foss North American/Tecator, Minneapolis, Minn.). After digestion, samples were cooled and diluted to a final volume of 100 mL with ammonia free water. Measurement of urinary and fecal nitrogen content was then conducted using a Technicon AutoAnalyzer II according to the manufacturer's protocols (Technicon Industrial Method No. 334-74W/B+, Technicon Industrial Systems, Tarrytown, N.Y.). All plasma samples were analyzed for ammonia (Sigma Tech. Bull. 171-UV, 1995, Sigma Chemical Co., St. Louis Mo.), urea nitrogen (Laborde et al., *Small Ruminant Research*, 17, 159–166 (1995)) and glucose (Sigma Tech. Bull. 315, 1989) using spectrophotometric procedures.

Trial 2.

Trial 2 was conducted with two replications using 40 Ts (average age=2.13 months) and 40 diploid (average age= 2.63 months) male mice. Replication 1 consisted of 24 Ts and 24 diploid mice and replication 2 consisted of 16 Ts and 16 diploid mice. Replicate experiments were conducted 4 weeks apart. Mice were randomly selected to receive either a s.c. injection of PYY (300 µg/kg body weight) or saline (0.9% NaCl) for three days. Mice were fasted 16 hours prior to being sedated for tissue and blood collection as described in Trial 1. Blood, liver, brain, epididymal fat pad and small and large intestine samples were collected as previously described. In addition, the small intestine lumen was flushed free of any residual digesta using HEPES buffer (pH 7.4, 25 mmol/L HEPES, 4.8 nmol/L KCL, 140 nmol/L NaCl, 2.5 nmol/L $CaCl_2$, 1.2 mmol/L Mg $SO_4$, 1.2 mmol/L $KH_2PO_4$). Two intestinal sections, 5 cm in length, proximal and distal to the midpoint of the jejunum were dissected. Eight rings of 1 mm thickness were cut from the proximal section using a cutting device made for this purpose (Bird et al., *J. Nutr.,* 124, 231–240 (1994)). The rings were placed in a petri dish containing HEPES buffer and stored on ice until utilized for the glucose transport assay. The distal jejunal section was cut into two pieces, 5 to 20 mg in weight, cut longitudinally, blotted dry, weighed and used immediately for measurement of tissue oxygen consumption.

Jejunal proline and both active and passive glucose uptake were measured by tissue accumulation of $^3$H-3-O-methyl-D-glucose ($^3$H-3OMG) and $^{14}$C-proline as described by Bird et al. (1994, 1996). Estimation of glucose and proline uptake of the entire intestine was calculated by multiplying glucose and proline uptake per gram of jejunal tissue by 50% of the total small intestine weight, as described by Fan et al., *J. Nutr.,* 126, 2851–2860 (1996).

Intact jejunal tissue $O_2$ uptake was measured according to the procedures described by Fan et al. (supra) for murine tissue using an oxygen monitor and incubation bath fitted with an oxygen electrode (YSI model 5300, Yellow Spring Instruments, Yellow Springs Ohio). Estimation of $O_2$ uptake of the entire jejunum was estimated by multiplying $O_2$ consumption rate per gram of jejunum by 50% of the small intestine weight as described by Fan et al. (supra). The APEE ($\eta$moles ATP expended/$\eta$moles glucose uptake) was determined as described by Bird et al. (supra) and Croom et al. *Can. J. Anim. Sci.,* 78, 1–13 (1998).

Mice brain samples were weighed in clean teflon liners and prepared for analysis by microwave digestion in low trace element grade nitric acid. Samples were then analyzed for Al content using Inductively Coupled Plasma Mass Spectrometry (Nuttall et al., *Annals of Clinical and Laboratory Science,* 25, 3, 264–271 (1995)). All tissue handling during analysis took place in a clean room environment utilizing HEPA air filtration systems to minimize background contamination. Brain Al pool values were calculated by multiplying sample Al concentration ($\mu$g/g) by the brain wet weight (g).

Data were analyzed by ANOVA using the General Linear Model procedure of SAS Institute Inc. (SAS/STAT® User's guide version 6.12. Cary N.C., SAS Inst. Inc. 1989). The main effects tested were replicate, mouse genotype, and treatment. Because the plasma ammonia and urea nitrogen data did not fit a normal distribution, these data were transformed and analyzed as logarithms. Simple correlation analysis was conducted between plasma ammonia and plasma urea nitrogen. Two mice brain Al concentration values were excluded from analysis because of suspected contamination as indicated by Al concentrations 4 to 40 times those in diploid and saline treated mice. Least square means and pooled SEM's are reported when unbalanced data were present.

B. Results

Trial 1.

There were no differences due to genotype or PYY in initial body weight, body weight gain during the trial or fasted body weight at the end of 14 days (Table 1). Small and large intestinal lengths were greater for diploid mice as compared to TS mice (P<0.05). No differences, however, were noted in small and large intestinal weights when adjusted to a fasted body weight (FBW) basis (Table 1). Ts65Dn epididymal fat pads were heavier (P<0.05) than their diploid littermates.

Peptide YY administration increased (P<0.05) small intestinal density (mg intestine/cm intestine length) as well as small intestinal weight adjusted for FBW (P<0.01) in both diploid and Ts mice. No other effects of PYY administration were noted in the intestines, brain, liver or epididymal fat pad.

Diploid mice consumed less food per gram FBW (P<0.05) than Ts mice, while PYY had no effects on any of the digestibility parameters measured (Table 2). No significant genotype differences were noted in ammonia, glucose or urea nitrogen (Table 3). A marked genotype X PYY interaction (P<0.01) was noted for both plasma glucose and plasma urea nitrogen. PYY administration increased plasma glucose in diploids compared to saline injected mice (13.74 vs. 10.98 mM, respectively) and decreased glucose in Ts mice (11.97 vs. 13.84 mM, Table 3). Conversely, PYY administration decreased plasma urea nitrogen concentrations compared to saline injected diploid mice (4.91 vs. 6.07 mM) while increasing urea nitrogen in Ts mice (6.04 vs. 5.41 mM).

Trial 2.

Ts65Dn mice had significantly lower FBWs (P<0.001) than their diploid controls (Table 4). The Ts mice had markedly shorter small intestinal (P<0.001) and large intestinal (P<0.05) lengths when compared to their non-trisomic controls. Similar to Trial 1, no significant differences were noted in either small or large intestinal weights when adjusted for FBW (Table 4). Both brain (P<0.001) and epididymal fat pad (P<0.05) weights were larger in the Ts mice than their controls after adjusting for FBW. The only significant effect of PYY administration on body weights and organ sizes was an increased large intestinal length (P<0.05) in both Ts and diploid mice.

Jejunal tissue glucose, proline, and oxygen uptake in Ts and diploid mice are presented in Table 5. There were no statistical differences between any of the variables measured due to either genotype or PYY administration. The APEE of jejunal glucose uptake, however, was lower (P<0.01) in diploid mice when compared to trisomic mice (FIG. 1).

Both genotype and PYY administration altered plasma metabolites in diploid and Ts mice (Table 6). Ts mice exhibited significantly elevated plasma ammonia levels (329 vs. 269 $\mu$M, p<0.05) and decreased plasma glucose levels (7.4 vs. 8.4 mM, p<0.01). A reduction in plasma urea nitrogen levels (P<0.05) in both genotypes was observed with PYY administration. Ts mice demonstrated a marked trend (P=0.06) for increased brain Al levels as compared to diploid mice. Peptide YY administration was associated with a non-significant trend (P=0.07) for reduction of brain Al concentration (ppm) and brain Al pools ($\mu$g) in both Ts and diploid mice. A decrease (p<0.05) in the brain Al pool adjusted for FBW was observed in all mice receiving PYY.

C. Discussion

As one attempts to integrate and interpret the data from Trials 1 and 2, it is apparent there are often differences regarding the statistical significance of various parameters common to both trials. It should be emphasized Trial 1 was designed to measure the effects of chronic administration (14 days) of PYY on nutrient digestibility while Trial 2 was designed to measure the effects of acute administration (3 days) on intestinal function and plasma metabolites. Additionally, Trial 1 utilized 24 mice individually kept in Nalgene® metabolism cages while Trial 2 included 80 mice each housed in a filtered polypropylene container.

A major paradox encountered when comparing whole body metabolism between diploid and Ts mice is the latter's smaller size (Cefalu et al., supra; Table 4), although they consume equal amounts (Cefalu et al. supra) or more food (Table 2) than their diploid controls. This could be explained partially by the hyperactivity of Ts mice (Cefalu et al., supra; Holtzman et al., supra) leading to increased energy expenditure. However, Cefalu et al. (supra) observed 24% lower whole-body oxygen uptake, corrected for activity, in Ts mice compared to controls. There were no differences in dry matter or energy digestibility between diploid and Ts mice (Table 2). These results are indicative of less efficient nutrient utilization by Ts mice than non-trisomic mice.

Bird et al. (supra) and Croom et al. (supra) have proposed the APEE as an indicator of the changes in energy requirements needed for nutrient absorption from the intestinal tract. Cefalu et al. (supra) reported an increased APEE in Ts mice and we report similar findings in the present study (FIG. 1). This suggests Ts mice require more energy to absorb glucose from the intestinal tract and may partially explain the discrepancy between increased energy and nitrogen intakes noted in Trial 1 and the generally smaller size of the Ts mice reported in Trial 2. The plausibility of this explanation is supported by the observations of Cant et al., *J. Anim. Sci.* 74, 2541–2553 (1996) that the gastrointestinal tract can account for as much as 20% of the total energy needs of animals. In Trial 2, Ts mice had lower fasting glucose levels (p<0.01), regardless of treatment, than their diploid controls. These results suggest differences in carbohydrate metabolism exist between Ts and diploid mice. Abnormalities in carbohydrate metabolism have been reported to occur at a higher frequency in DS individuals than in diploid controls (Pueschel and Anneren, in *Biomedical Concerns in Persons with Downs Syndrome*, chap. 23 (Pueschel & Pueschel Eds. 992)).

The Ts mice in Trials 1 and 2 had epididymal fat pads that were 41 and 34% heavier than controls, respectively. Eisen and Leatherwood *J. Nutr.* 108, 1663–1672 (1978) have reported epididymal fat pad weight to be highly correlated with whole-body fat percent in mice selected for rapid growth. These observations support the conclusions of Davisson et al. (supra) that 4 to 6 months old Ts mice exhibit early onset obesity as compared to diploid controls. The propensity of Ts mice to have more body fat may speak to inefficiencies in their ability to convert dietary protein to muscle. This may explain the decreased whole-body $O_2$ consumption noted by Cefalu et al. (supra).

Anomalies in nitrogen metabolism may also contribute to differences in whole-body energy metabolism between Ts and diploid mice. Plasma ammonia concentrations were elevated 27% in Ts mice in Trial 2, while non-significant trends were noted in Trial 1. Cefalu et al. (supra) reported significant increases in circulating levels of ornithine, citrulline and the branched chain amino acids (BCAA) in Ts mice. Similar to data previously reported in humans (Miga and Roth, 1993), circulating levels of blood urea nitrogen were not highly correlated (r=0.07) with hyperammonemia in Trials 1 or 2. These data suggest disposal of ammonia, as the result of deamination and other transformation reactions involving amino acids, is impaired in the Ts mouse. HHH syndrome (Hyperornithinemia, Hyperammonemia and Homocitrullinuria) is characterized by protein intolerance, mental retardation, seizures, and episodic attacks of ataxia and lethargy (Shih et al., *J. Inher. Metab. Dis.*, 4, 95–96 (1981)). The cause of this syndrome is believed to be a defect in mitochondrial transport of ornithine (Shih et al., supra). This may explain, in part, the hyperammonemia observed in the Ts mice.

Davisson et al. (supra) observed hydrocephalus in Ts mice. Increased brain weights of Ts mice as compared to diploid controls in the present study as well as that of Cefalu et al. (supra) support this observation. Hyper-ammonemia, through concomitant increases in glutamine concentrations, has been reported to cause brain swelling in rats (Takahashi et al., *Am. J. Physiol.*, 261, 3Pt2, H825–829 (1991)). Hyperammonemia could be causing the hydrocephalus and increased brain weights of Ts mice.

Peptide YY failed to enhance the intestinal uptake of either glucose or proline in diploid and Ts mice (Table 5). Similarly, PYY failed to affect the apparent digestibility of any nutrients (Table 2). These are contrary to previous studies in our laboratory, which have described increased intestinal glucose uptake in Swiss Webster mice treated with PYY (Bird et al., supra). Furthermore, Coles et al. *Poultry Science*, 76, (Suppl. 1), 71. (abstr.) (1997) have described increased jejunal glucose uptake in Nicholas and Egg Line turkey poults hatched from eggs treated in ovo with 600 μg PYY/kg egg weight, three days before hatch. The failure to enhance intestinal glucose absorption in the present study may be due to genotypic differences among mice strains, since studies in our laboratory have noted differences regarding the effects of PYY on intestinal glucose absorption in different strains of turkey poults (B. A. Coles et al., unpublished observations).

Goodlad et al. *Digestion*, 46, Suppl. 2, 177–81 (1990) reported administration of PYY to rats for 3 days had no effect on intestinal cell proliferation. Conversely, PYY has been noted to have trophic effects on the intestinal tract in vivo when administered for 7 days (Chance et al., *Nutrition*, 14, 6, 502–507 (1998)). In Trial 1, chronic PYY administration increased small intestinal density (mg/cm) in both genotypes. It is clear from these data that PYY can alter intestinal morphology. Cefalu et al. (supra) reported shorter and thinner jejunal villi and shorter small intestine lengths in Ts mice when compared to diploid controls. Like Cefalu et al. (supra), we also found shorter small intestines and additionally observed shorter large intestines in the Ts mice when compared to diploids.

Neuropathological markers of AD such as degenerating basal forebrain cholinergic neurons (BFCNs) and astrocytic hypertrophy, have been isolated in Ts mice brains (Holtzman et al., supra), while neuritic plaques and tangles have not been detected in Ts mice brains (Reeves et al. supra). Increased central nervous system accretion of Al has been proposed in the etiology of AD (Deloncle and Guillard, *Neurochemical Research*, 15, 12, 1239–1245 (1990); Forbes and Hill, *Arch. Neurol.*, May, 55, 5, 740–741 (1998); Savory et al.,supra), although others dispute this hypothesis (Munoz, *Arch Neurol*, 55, 5, 737–739 (1998); Bjertness et al., *Alzheimer Disease & Associated Disorders*, 10, 3, 171–174 (1996)). In Trial 2, Ts mice receiving saline had 3.5 times higher brain Al concentrations (ppm) on a wet weight basis than diploids administered saline. The range of values we observed (0.007 to 2.52 ppm) were similar to values reported by Deloncle et al. (supra) in control and aluminum-glutamate treated rats.

Alzheimer's patients have been described as having post prandial hyperammonemia, which may be involved in the etiology of this disease (Seiler, *Neurochemical Research*, 18, 3, 235–245 (1993)). Ts65Dn mice appear hyperammonemic (Table 6). Deloncle and Guillard (supra) have proposed elevated levels of Al complex with brain glutamate and decrease its rate of conversion to glutamine. Inhibition of this metabolic reaction may in turn hamper the brain's ability to buffer against increased ammonia concentration, which may be responsible for neuronal death during AD (Deloncle and Guillard, supra). In a later study, Deloncle et al. *Biol. Trace Elem. Res.*, 47, 227–233 (1995) reported oral and intravenous infusions of aluminum-glutamate increased accumulation of aluminum in various parts of the brain. The study of brain Al, ammonia, and glutamate interactions in Ts mice may help characterize the mechanisms of neuronal damage in AD.

Both diploid and Ts mice receiving exogenous PYY had 44 and 68% lower brain Al concentrations (ppm), respectively, than their non-treated counterparts. Similarly, brain aluminum pools adjusted for FBW were lower ($p<0.05$) in both diploid and Ts mice treated with PYY. To our knowledge, this is the first study to describe the ability of PYY to deplete the central nervous system of Al. It is not clear if PYY's effect is primary or represents one step in a metabolic cascade. PYY has been administered to humans intravenously and tolerated well (Savage et al., *Gut.*, 28, 166–170 (1987)). These results suggest Ts mice and PYY may serve as useful tools for the study and treatment of AD and other aluminum related diseases in humans.

When considered as a whole, the data in the present study supports the observations of Cefalu et al. (supra) that the Ts mouse may serve as a useful metabolic model for Down syndrome. This position supports a recent review of DS mouse models by Kola and Hertzog (supra). The similarities in behavioral and metabolic parameters between DS patients and Ts mice have been summarized in Table 7. Furthermore, observations made in this study and those of Cefalu et al. (supra) of differences in metabolism between diploid and Ts mice strengthen arguments that Down syndrome patients may have different metabolism and nutrient requirements than those of the general population (Anonymous, *J. of the American Dietetic Association*, 97, 187–193 (1997); Coburn et al., *Am. J. Clin. Nutr.*, 38, 352–355 (1983); Sylvester, *British Journal of Psychiatry*, 145, 115–120 (1984)).

TABLE 1

Trial I: Body weights and organ sizes[a]

| Variables | Diploid Saline | Diploid PYY | Ts65Dn Saline | Ts65Dn PYY | SEM | Significance[b] |
|---|---|---|---|---|---|---|
| Initial body weight, g | 23.97 | 23.23 | 22.55 | 20.59 | 1.18 | NS |
| Body weight gain, g | 1.74 | 2.51 | 2.18 | 1.39 | 0.60 | NS |
| Fasted body weight (FBW)[c], g | 25.70 | 25.74 | 24.73 | 21.99 | 1.17 | NS |
| Small intestine length, cm | 33.63 | 36.13 | 32.58 | 30.68 | 1.47 | A* |
| Small intestine density, mg/cm | 22.23 | 25.10 | 21.83 | 24.95 | 1.22 | B* |
| Large intestine length, cm | 8.52 | 8.37 | 7.78 | 7.20 | 0.42 | A* |
| Large intestine density, mg/cm | 21.21 | 24.42 | 23.74 | 23.87 | 1.89 | NS |
| mg/g (FBW)[d] | | | | | | |
| Brain | 17.46 | 18.12 | 16.22 | 19.58 | 1.30 | NS |
| Epididymal fat pad | 17.43 | 13.83 | 26.11 | 17.88 | 2.90 | A* |
| Liver | 47.82 | 52.41 | 51.70 | 54.80 | 3.07 | NS |
| Small intestine | 29.32 | 35.17 | 29.04 | 34.60 | 1.73 | B** |
| Large intestine | 7.12 | 7.91 | 7.42 | 7.87 | 0.65 | NS |

[a]Values are least square means, n = 6 diploid saline, n = 6 diploid PYY, n = 6 Ts65Dn saline, n = 6 Ts65Dn PYY
[b]A = Genotype
B = PYY
NS p value > 0.05
* p value ≦ 0.05
** p value ≦ 0.01
[c]FBW = Weight of mice after 16-h food deprivation
[d]mg/g FBW = mg organ weight per gram whole body weight after 16-h food deprivation

TABLE 2

Trial 1: Nutrient digestibility[a]

| Variables | Diploid Saline | Diploid PYY | Ts65Dn Saline | Ts65Dn PYY | SEM | Significance[b] |
|---|---|---|---|---|---|---|
| Feed intake, g dry matter/day/g FBW | 0.15 | 0.15 | 0.16 | 0.17 | 0.005 | A* |
| Water intake, ml/g FBW | 0.19 | 0.24 | 0.23 | 0.24 | 0.023 | NS |
| Energy intake, kcal/day/g FBW | .6412 | .6315 | .6682 | .7176 | .0209 | A** |
| Nitrogen intake, mg/day/g FBW | 5.08 | 5.00 | 5.28 | 5.74 | .1716 | A** |
| Fecal output, g dry matter/day/g FBW | 0.07 | 0.06 | 0.06 | 0.07 | 0.004 | NS |
| Fecal dry matter, % | 93.10 | 92.86 | 93.85 | 93.00 | 0.1206 | NS |
| Dry matter digestibility, % | 57.21 | 58.73 | 59.54 | 56.85 | 16.31 | NS |
| Dry matter retention, mg/g FBW | 1.30 | 1.31 | 1.41 | 1.26 | 0.105 | NS |
| Fecal energy, kcal/day/g FBW | .3020 | .2863 | .2954 | .3429 | 0.017 | NS |
| Digestible energy, % | 53.19 | 54.89 | 55.95 | 52.16 | 1.83 | NS |
| Energy retention, kcal/g FBW | 5.09 | 5.18 | 5.59 | 4.81 | .403 | NS |
| Urine output, ml/day/g FBW | 0.031 | 0.061 | 0.033 | 0.024 | 0.010 | NS |
| Urinary nitrogen, mg/day/g FBW | 2.22 | 3.06 | 2.15 | 2.00 | .383[c] | NS |

TABLE 2-continued

Trial 1: Nutrient digestibility[a]

| | Diploid | | Ts65Dn | | | |
|---|---|---|---|---|---|---|
| Variables | Saline | PYY | Saline | PYY | SEM | Significance[b] |
| Fecal nitrogen, mg/day/g FBW | 2.34 | 2.14 | 2.28 | 2.89 | 0.2411 | NS |
| Nitrogen balance, mg/g FBW | 14.50 | −0.24 | 13.74 | 2.41 | 7.73[c] | NS |

Values are least square means, n = 6 diploid saline, n = 6 diploid PYY, n = 6 Ts65Dn saline, n = 6 Ts65Dn PYY

[b]A = Genotype

NS p value > 0.05

\* p value $\leq$ 0.05

\*\* p value $\leq$ 0.01

[c]Values are pooled SEMs

TABLE 3

Trial 1: Plasma metabolites[a]

| | Diploid | | Ts65Dn | | | Signifi- |
|---|---|---|---|---|---|---|
| Variables | Saline | PYY | Saline | PYY | SEM | cance[b] |
| Ammonia, uM[c] | 170.0 | 186.1 | 234.5 | 217.8 | 40.3 | NS |
| Glucose, mM[d] | 11.0 | 13.7 | 13.8 | 12.0 | 0.81[e] | C\*\* |
| Urea nitrogen, mM[c,d] | 6.1 | 4.9 | 5.4 | 6.0 | 0.31[e] | C\*\* |

[a]Values are least square means, n = 6 diploid saline, n = 6 diploid PYY, n = 6 Ts65Dn saline, n = 6 Ts65Dn PYY.

[b]C = Genotype X PYY

NS p value > 0.05

\*\* p value $\leq$ 0.01

[c]Log transformation was required for statistical analysis. Values represent anti-logs of analyzed data.

[d]n = 6 diploid saline, n = 5 diploid PYY, n = 6 Ts65Dn saline, n = 6 Ts65Dn PYY

[e]Values are pooled SEMs.

TABLE 4

Trial 2: Body weights and organ sizes[a]

| | Diploid | | Ts65Dn | | | Signifi- |
|---|---|---|---|---|---|---|
| Variables | Saline | PYY | Saline | PYY | SEM | cance[b] |
| Fasted body weight (FBW), g | 23.07 | 24.74 | 21.45 | 20.74 | 0.739[c] | A\*\*\* |
| Small intestine length, cm | 32.68 | 33.95 | 30.73 | 30.51 | 0.700 | A\*\*\* |
| Small intestine density, mg/cm | 26.33 | 26.97 | 26.19 | 25.01 | 1.01 | NS |
| Large intestine length, cm | 6.07 | 7.01 | 6.18 | 6.63 | 0.202 | A\*, B\* |
| Large intestine density, mg/cm | 27.42 | 29.38 | 26.70 | 26.48 | 1.41 | NS |
| mg/g (FBW) | | | | | | |
| Brain | 18.36 | 17.02 | 20.21 | 20.61 | 0.698[c] | A\*\*\* |
| Epididymal fat pad | 13.48 | 15.24 | 20.47 | 18.03 | 2.39[c] | A\* |
| Liver | 41.40 | 40.14 | 42.69 | 43.35 | 1.27[c] | NS |
| Small intestine | 37.76 | 37.10 | 37.99 | 37.16 | 1.28[c] | NS |
| Large intestine | 8.06 | 8.30 | 7.87 | 8.25 | 0.455[c] | NS |

[a]Values are least square means, n = 20 diploid saline, n = 20 diploid PYY, n = 20 Ts65Dn saline, n = 20 Ts65Dn PYY

[b]A = Genotype

B = PYY

NS p value > 0.05

\* p value $\leq$ 0.05

\*\*\* p value $\leq$ 0.001

[c]Values are pooled SEMs, n = 19 diploid saline, n = 20 diploid PYY, n = 19 Ts65Dn saline, n = 20 Ts65Dn PYY

TABLE 5

Trial 2: Jejunal glucose, proline and oxygen uptake[a]

| | Diploid | | Ts65Dn | | | |
|---|---|---|---|---|---|---|
| Variables | Saline | PYY | Saline | PYY | SEM | Significance[b] |
| Jejunal segment, pmol/min/mg tissue | | | | | | |
| Active glucose uptake[c] | 203.87 | 218.04 | 201.27 | 210.42 | 26.03[d] | NS |
| Passive glucose uptake[e] | 54.84 | 70.64 | 68.27 | 78.31 | 9.00[d] | NS |
| Total glucose uptake[f] | 253.92 | 290.27 | 264.25 | 288.12 | 26.10[d] | NS |
| Proline uptake[g] | 325.02 | 283.67 | 285.65 | 314.76 | 47.16 | NS |
| Adjusted entire jejunum[b], pmol/min/g FBW | | | | | | |
| Active glucose uptake | 3.72 | 4.06 | 3.97 | 4.09 | 0.4973 | NS |
| Passive glucose uptake | 1.07 | 1.34 | 1.34 | 1.47 | 0.1825 | NS |
| Total glucose uptake | 4.90 | 5.18 | 5.17 | 5.36 | 0.5233 | NS |
| Proline uptake | 12.18 | 9.66 | 10.68 | 11.77 | 2.02 | NS |
| Jejunal segment O$_2$, ηmol/min/mg wet tissue | 1.29 | 1.17 | 1.47 | 1.16 | 0.1513 | NS |

TABLE 5-continued

Trial 2: Jejunal glucose, proline and oxygen uptake[a]

| | Diploid | | Ts65Dn | | | |
|---|---|---|---|---|---|---|
| Variables | Saline | PYY | Saline | PYY | SEM | Significance[b] |
| Adjusted entire jejunum $O_2$[h], ηmol/min/g FBW | 24.58 | 21.84 | 27.29 | 21.67 | 2.67 | NS |

[a]Values are least square means.
[b]NS p value > 0.05
[c]n = 20 diploid saline, n = 19 diploid PYY, n = 20 Ts65Dn saline, n = 19 Ts65Dn PYY
[d]Values are pooled SEM's.
[e]n = 18 diploid saline, n = 20 diploid PYY, n = 18 Ts65Dn saline, n = 19 Ts65Dn PYY
[f]n = 18 diploid saline, n = 19 diploid PYY, n = 18 Ts65Dn saline, n = 19 Ts65Dn PYY
[g]n = 8 diploid saline, n = 8 diploid PYY, n = 8 Ts65Dn saline, n = 8 Ts65Dn PYY.
[h]adjusted values = (jejunal rate × 50% small intestine weight)/g FBW.

TABLE 6

Trial 2: Plasma metabolites and brain aluminum[a]

| | Diploid | | Ts65Dn | | | |
|---|---|---|---|---|---|---|
| Variables | Saline | PYY | Saline | PYY | SEM[b] | Significance[c] |
| Ammonia, μM[de] | 268.9 | 280.4 | 328.6 | 342.90 | 33.6 | A*** |
| Glucose, mM[f] | 8.4 | 8.2 | 7.4 | 6.1 | 0.60 | A**** |
| Urea nitrogen, mM[dg] | 7.7 | 6.4 | 7.2 | 6.7 | 0.46 | B*** |
| Aluminum, ppm[h] | 0.304 | 0.164 | 1.05 | 0.333 | 0.22 | A**, B* |
| Brain aluminum pool, μg[h] | 0.117 | 0.066 | 0.410 | 0.133 | 0.08 | A**, B* |
| Adjusted brain aluminum pool, μg/g FBW[h] | 0.019 | 0.0026 | 0.024 | 0.0065 | 0.008 | B*** |

[a]Values are least square means.
[b]Values are pooled SEMs.
[c]A = Genotype
B = PYY
*p value ≦ 0.08
**p value ≦ 0.06
***p value ≦ 0.05
****p value ≦ 0.01
[d]Log transformation was required for statistical analysis. Values represent anti-logs of analyzed data.
[e]n = 19 diploid saline, n = 16 diploid PYY, n = 19 Ts65Dn saline, n = 20 Ts65Dn PYY
[f]n = 19 diploid saline, n = 20 diploid PYY, n = 18 Ts65Dn saline, n = 20 Ts65Dn PYY
[g]n = 19 diploid saline, n = 20 diploid PYY, n = 19 Ts65Dn saline, n = 19 Ts65Dn PYY
[h]n = 5 diploid saline, n = 7 diploid PYY, n = 6 Ts65Dn saline, n = 5 Ts65Dn PYY

TABLE 7

Characteristics common to Down syndrome (DS) individuals and Ts65Dn mice.

| Characteristics | DS Humans | DS model (Ts65Dn) |
|---|---|---|
| Growth | | |
| Early development delay | Epstein(1989)<br>Cronk & Anneren(1992) | Davisson et al.(1993)<br>Holtzman et al.(1996)<br>Cefalu et al.(1998) |
| Behavior | | |
| Hyperactivity | Pueschel et al.(1991)<br>Luke et al.(1994) | Escorihuela et al.(1995)<br>Reeves et al.(1995)<br>Cefalu el al.(1998) |
| Metabolism | | |
| BMR/RMR | Chad et al.(1990) - decreased (indirect comparison)<br>Roizen et al.(1995) - decreased<br>Luke et al.(1994) - decreased | Cefalu et al.(1998) - decreased |
| Plasma amino acid levels | Watkins et al.(1989) - increased branched chain amino acids | Cefalu et al.(1998) - increased branched chain amino acids |
| AD-like Neuro-pathology | Lai and Williams, 1989<br>Lott, 1982<br>Schupf et al.,1998 | Holtzman et al.(1996) - neurodegeneration |

ADDITIONAL REFERENCES

CHAD, K., et al., 1990, *American Journal on Mental Retardation*, 95, 2, 228–235.

CRONK, C. E., & ANNEREN, G. 1992, In: Biomedical Concerns in Persons With Down Syndrome. (eds. Pueschel, S. M., & Pueschel, J. K.), pp.19–37. Baltimore, Md.: Paul H. Brookes Publishing Co.

EPSTEIN, C. J. 19989 In: The Metabolic Basis of Inherited Disease. (eds. Shriver, R. C., Beaudet, A. L., Sly, W. S., & Valle, D.), sixth edition. Vol I. pp.291–326. New York, N.Y.: McGraw Hill Inc.

LAI, F., et al., 1989, *Arch. Neurol.,* 46, 849–853.

LOTT, I. T. 1982, *Annals of the New York Academy of Sciences,* 396, 15–27.

LUKE, A. et al., 1994. *J. Pediatr.,* 125, 829–838.

MIGA, D. E., & ROTH, K. S., 1993, *Southern Medical Journal,* 86, 7, 742–747.

PUESCHEL, S. M., et al., 1991, *J. Ment. Defic. Res.,* 35, 502–511.

ROIZEN, N. J. et al., 1995, In: Down Syndrome Living and Learning in the Community. (eds. Nadel, L. & Rosenthal, D.), pp.213–215. New York, N.Y.: Wiley-Liss Inc.

WATKINS, S. E. et al., 1989, *J. Ment. Def. Res.,* 33, 159–166.

The foregoing is illustrative of the present invention, and is not to be construed as limiting thereof. The invention is defined by the following claims, with equivalents of the claims to be included therein.

What is claimed is:

1. A method of treating dialysis dementia in a subject diagnosed with dialysis dementia, comprising administering to said subject a Protein YY (PYY) receptor agonist in an amount effective to reduce aluminum levels in the central nervous system of said subject, wherein a reduction in aluminum level can be correlated with a decrease in plasma urea nitrogen level.

2. The method according to claim 1, wherein said administering step is a parenteral administration step.

3. The method according to claim 1, wherein said administering step is an oral administration step.

4. The method according to claim 1, wherein said administering step is a nasal or inhalation administration step.

5. The method according to claim 1, wherein said PYY receptor agonist is mammalian PYY or a pharmaceutically acceptable salt thereof.

6. The method according to claim 1, wherein said PYY receptor agonist is selected from the group consisting of porcine PYY, human PYY, and the pharmaceutically acceptable salts thereof.

7. The method according to claim 1, wherein said a PYY receptor agonist is administered in an amount effective to reduce aluminum levels in the brain of said subject.

8. The method according to claim 1, wherein said PYY receptor agonist is a compound of the formula:

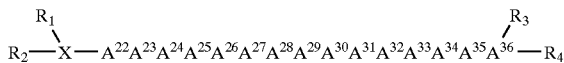

wherein:

X is Cys or is deleted;

each of $R_1$ and $R_2$ is bonded to the nitrogen atom of the α-amino group of the N-terminal amino acid;

$R_1$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$R_2$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$A^{22}$ is an aromatic amino acid, Ala, aminoisobutyric acid (Aib) α-aminonormalbutyric acid (Anb), N-Me-Ala, or is deleted;

$A^{23}$ is Ser, Thr, Ala, Aib, N-Me-Ser, N-Me-Thr, N-Me-Ala, D-Trp, or is deleted;

$A^{24}$ is Leu, Gly, Ile, Val, Norleucine (Nle), Norvaline (Nva), Anb, N-Me-Leu, or is deleted;

$A^{25}$ is Arg, Lys, homo-Arg, diethyl-homo-Arg, Lys-ε-NH—R (where R is H, a branched or straight chain C1–C10 alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-β-NH—R (where R is H, a branched or straight chain $C_1$–$C_{10}$ alkyl group, or an aryl group), Orn, or is deleted;

$A^{27}$ is 2-napthylalanine (Nal), 4,4'-biphenylalanine (Bip), 4-chlorophenylalanine (Pcp), tetrahydroisoquinoline-3-carboxylic acid (Tic), Trp, 3-benzothienyalanine (Bth), 2-thienylalanine (Thi), or 2,2-diphenylalanine (Dip);

$A^{28}$ is Leu, Val, Trp, Nle, Nva, Aib, Anb, or N-Me-Leu;

$A^{29}$ is Asn, Ala, Gln, Gly, Trp, or N-Me-Asn;

$A^{30}$ is Leu, Ile, Val, Trp, Nle, Nva, Aib, Anb, or N-Me-Leu;

$A^{31}$ is Val, Leu, Ile, Trp, Nle, Nva, Aib, Anb, or N-Me-Val;

$A^{32}$ is Thr, Ser, N-Me-Ser, N-Me-Thr, or D-Trp;

$A^{33}$ is Cys, Arg, Lys, homo-Arg, diethyl-homo-Arg, Lys-ε.-NH—R (where R is H, a branched or straight chain $C_1$–$C_{10}$ alkyl group, or $C_6$–$C_{18}$ aryl group), or Orn;

$A^{34}$ is Cys, Gln, Asn, Ala, Gly, N-Me-Gln, Aib, or Anb;

$A^{35}$ is Cys, Arg, Lys, homo-Arg, diethyl-homo-Arg, Lys-ε-NH—R (where R is H, a branched or straight chain $C_1$–$C_{10}$ alkyl group, or $C_6$–$C_{18}$ aryl group), or Orn;

$A^{36}$ is an aromatic amino acid, or Cys;

$R_3$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl; and $R_4$ is H, $C_1$–$C_{C12}$ alkyl, $C_6$–$C_{18}$ aryl, $C_1$–$C_{12}$ acyl, $C_7$–$C_{18}$ aralkyl, or $C_7$–$C_{18}$ alkaryl;

or a pharmaceutically acceptable salt thereof.

9. The method according to claim 1, wherein said PYY receptor agonist is selected from the group consisting of:

N-α-Ac-Ala-Ser-Leu-Arg-His-Phe-Leu-Asn-Leu-Val-Thr-Arg-Gln-Arg-Tyr-NH₂ (SEQ ID NO: 3);

H-Ala-Ser-Leu-Arg-His-Phe-Leu-Asn-Leu-Val-Thr-Arg-Gln-Arg-Tyr-NH₂ (SEQ ID NO: 4);

N-α-Ac-Ala-Ser-Leu-Arg-His-Trp-Leu-Asn-Leu-Val-Thr-Arg-Gln-Arg-Tyr-NH₂ (SEQ ID NO: 5);

N-α-Ac-Ala-Ser-Leu-Arg-His-Thi-Leu-Asn-Leu-Val-Thr-Arg-Gln-Arg-Tyr-NH₂ (SEQ ID NO: 6);

N-α-Ac-Tyr-Ser-Leu-Arg-His-Phe-Leu-Asn-Leu-Val-Thr-Arg-Gln-Arg-Tyr-NH₂ (SEQ NO: 7);

N-α-Ac-Arg-His-Phe-Leu-Asn-Leu-Val-Thr-Arg-Gln-Arg-Tyr-NH₂ (SEQ ID NO: 8);

and the pharmaceutically acceptable salts thereof.

10. A method of treating Alzheimer's disease in a subject at risk of developing Alzheimer's disease or having a probable diagnosis of Alzheimer's disease, comprising administering to said subject a PYY receptor agonist in an amount effective to reduce aluminum levels in the central nervous system of said subject, wherein a reduction in aluminum level can be correlated with a decrease in plasma urea nitrogen level.

11. The method according to claim 10, wherein said PYY receptor agonist is administered in an amount effective to reduce aluminum levels in the brain of said subject.

12. The method according to claim 10, wherein said administering step is a parenteral administration step.

13. The method according to claim 10, wherein said administering step is an oral administration step.

14. The method according to claim 10, wherein said administering step is a nasal or inhalation administration step.

15. The method according to claim 10, wherein said PYY receptor agonist is mammalian PYY or a pharmaceutically acceptable salt thereof.

16. The method according to claim 10, wherein said PYY receptor agonist is selected from the group consisting of porcine PYY, human PYY, and the pharmaceutically acceptable salts thereof.

17. The method according to claim 10, wherein said a PYY receptor agonist is administered in an amount effective to reduce aluminum levels in the brain of said subject.

18. The method according to claim 10, wherein said PYY receptor agonist is a compound of the formula:

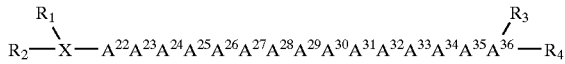

wherein:

X is Cys or is deleted;

each of $R_1$ and $R_2$ is bonded to the nitrogen atom of the α-amino group of the N-terminal amino acid;

$R_1$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$R_2$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$A^{22}$ is an aromatic amino acid, Ala, Aib, Anb, N-Me-Ala, or is deleted;

$A^{23}$ is Ser, Thr, Ala, Aib, N-Me-Ser, N-Me-Thr, N-Me-Ala, D-Trp, or is deleted;

$A^{24}$ is Leu, Gly, Ile, Val, Trp, Nle, Nva, Aib, Anb, N-Me-Leu, or is deleted;

$A^{25}$ is Arg, Lys, homo-Arg, diethyl-homo-Arg, Lys-ε-NH—R (where R is H, a branched or straight chain C1–C10 alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain C1–C10 alkyl group, or an aryl group), Orn, or is deleted;

$A^{27}$ is Nal, Bip, Pcp, Tic, Trp, Bth, Thi, or Dip;

$A^{28}$ is Leu, Val, Trp, Nle, Nva, Aib, Anb, or N-Me-Leu;

$A^{29}$ is Asn, Ala, Gln, Gly, Trp, or N-Me-Asn;

$A^{30}$ is Leu, Ile, Val, Trp, Nle, Nva, Aib, Anb, or N-Me-Leu;

$A^{31}$ is Val, Leu, Ile, Trp, Nle, Nva, Aib, Anb, or N-Me-Val;

$A^{32}$ is Thr, Ser, N-Me-Ser, N-Me-Thr, or D-Trp;

$A^{33}$ is Cys, Arg, Lys, homo-Arg, diethyl-homo-Arg, Lys-ϵ-NH—R (where R is H, a branched or straight chain $C_1$–$C_{10}$ alkyl group, or $C_6$–$C_{18}$ aryl group), or Orn;

$A^{34}$ is Cys, Gln, Asn, Ala, Gly, N-Me-Gln, Aib, or Anb;

$A^{35}$ is Cys, Arg, Lys, homo-Arg, diethyl-homo-Arg, Lys-ϵ-NH—R (where R is H, a branched or straight chain $C_1$–$C_{10}$ alkyl group, or $C_6$–$C_{18}$ aryl group), or Orn;

$A^{36}$ is an aromatic amino acid, or Cys;

$R_3$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl; and $R_4$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

or a pharmaceutically acceptable salt thereof.

19. The method according to claim 10, wherein said PYY receptor agonist is selected from the group consisting of:

N-α-Ac-Ala-Ser-Leu-Arg-His-Phe-Leu-Asn-Leu-Val-Thr-Arg-Gln-Arg-Tyr-$NH_2$ (SEQ ID NO: 3);

H-Ala-Ser-Leu-Arg-His-Phe-Leu-Asn-Leu-Val-Thr-Arg-Gln-Arg-Tyr-$NH_2$ (SEQ ID NO: 4);

N-α-Ac-Ala-Ser-Leu-Arg-His-Trp-Leu-Asn-Leu-Val-Thr-Arg-Gln-Arg-Tyr-$NH_2$ (SEQ ID NO: 5);

N-α-Ac-Ala-Ser-Leu-Arg-His-Thi-Leu-Asn-Leu-Val-Thr-Arg-Gln-Arg-Tyr-$NH_2$ (SEQ ID NO: 6);

N-α-Ac-Tyr-Ser-Leu-Arg-His-Phe-Leu-Asn-Leu-Val-Thr-Arg-Gln-Arg-Tyr-$NH_2$ (SEQ ID NO: 7);

N-α-Ac-Arg-His-Phe-Leu-Asn-Leu-Val-Thr-Arg-Gln-Arg-Tyr-$NH_2$ (SEQ ID NO: 8);

the pharmaceutically acceptable salts thereof.

\* \* \* \* \*

UNITED STATES PATENT AND TRADEMARK OFFICE
CERTIFICATE OF CORRECTION

PATENT NO.    : 6,734,166 B1
DATED         : May 11, 2004
INVENTOR(S)   : Croom, Jr. et al.

It is certified that error appears in the above-identified patent and that said Letters Patent is hereby corrected as shown below:

Column 10,
Line 24, should read -- In particular embodiments of the foregoing $A^{27}$ is Phe, --
Lines 26-28, should read -- In particular embodiments of the foregoing Y is $A^{33}$-$A^{34}$-$A^{35}$-$A^{36}$ wherein $A^{33}$ is Arg, Lys, homo-Arg, diethyl-homo-Arg, Lys-. --

Column 30,
Line 63, should read -- 7. The method according to claim 1, wherein said PYY --

Column 31,
Line 20, should read -- $A^{24}$ is Leu, Gly, Ile, Val, Trp, Norleucine (Nle), Norvaline --
Line 29, should read -- diethyl-homo-Arg, Lys-ε-NH-R (where R is H, a --
Line 56, should read -- $R_4$ is H, $C_1$-$C_{12}$ alkyl, $C_6$-$C_{18}$ aryl, $C_1$-$C_{12}$ acyl, $C_7$-$C_{18}$ --

Column 32,
Line 35, should read -- 17. The method according to claim 10, wherein said --

Signed and Sealed this

Fifth Day October, 2004

JON W. DUDAS
*Director of the United States Patent and Trademark Office*

SEQUENCE LISTING

```
<160> NUMBER OF SEQ ID NOS: 8

<210> SEQ ID NO 1
<211> LENGTH: 36
<212> TYPE: PRT
<213> ORGANISM: Sus scrofa

<400> SEQUENCE: 1

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35

<210> SEQ ID NO 2
<211> LENGTH: 36
<212> TYPE: PRT
<213> ORGANISM: Homo sapiens

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 15
<212> TYPE: PRT
<213> ORGANISM: synthetic construct
<220> FEATURE:
<221> NAME/KEY: MOD_RES
<222> LOCATION: (1)..(1)
<223> OTHER INFORMATION: N-Alpha-(C1-C12) Acyl Group Modification

<400> SEQUENCE: 3

Ala Ser Leu Arg His Phe Leu Asn Leu Val Thr Arg Gln Arg Tyr
1               5                   10                  15

<210> SEQ ID NO 4
<211> LENGTH: 15
<212> TYPE: PRT
<213> ORGANISM: synthetic construct

<400> SEQUENCE: 4

Ala Ser Leu Arg His Phe Leu Asn Leu Val Thr Arg Gln Arg Tyr
1               5                   10                  15
```

```
<210> SEQ ID NO 5
<211> LENGTH: 15
<212> TYPE: PRT
<213> ORGANISM: synthetic construct
<220> FEATURE:
<221> NAME/KEY: MOD_RES
<222> LOCATION: (1)..(1)
<223> OTHER INFORMATION: N-Alpha-(C1-C12) Acyl Group Modification

<400> SEQUENCE: 5

Ala Ser Leu Arg His Trp Leu Asn Leu Val Thr Arg Gln Arg Tyr
1               5                   10                  15

<210> SEQ ID NO 6
<211> LENGTH: 15
<212> TYPE: PRT
<213> ORGANISM: synthetic construct
<220> FEATURE:
<221> NAME/KEY: MOD_RES
<222> LOCATION: (1)..(1)
<223> OTHER INFORMATION: N-Alpha-(C1-C12) Acyl Group Modification
<221> NAME/KEY: MOD_RES
<222> LOCATION: (6)..(6)
<223> OTHER INFORMATION: 2-Thienylalanine

<400> SEQUENCE: 6

Ala Ser Leu Arg His Ala Leu Asn Leu Val Thr Arg Gln Arg Tyr
1               5                   10                  15

<210> SEQ ID NO 7
<211> LENGTH: 15
<212> TYPE: PRT
<213> ORGANISM: synthetic construct
<220> FEATURE:
<221> NAME/KEY: MOD_RES
<222> LOCATION: (1)..(1)
<223> OTHER INFORMATION: N-Alpha-(C1-C12) Acyl Group Modification

<400> SEQUENCE: 7

Tyr Ser Leu Arg His Phe Leu Asn Leu Val Thr Arg Gln Arg Tyr
1               5                   10                  15

<210> SEQ ID NO 8
<211> LENGTH: 12
<212> TYPE: PRT
<213> ORGANISM: synthetic construct
<220> FEATURE:
<221> NAME/KEY: MOD_RES
<222> LOCATION: (1)..(1)
<223> OTHER INFORMATION: N-Alpha-(C1-C12) Acyl Group Modification

<400> SEQUENCE: 8

Arg His Phe Leu Asn Leu Val Thr Arg Gln Arg Tyr
1               5                   10
```